United States Patent
Kim et al.

(10) Patent No.: US 8,655,678 B2
(45) Date of Patent: Feb. 18, 2014

(54) MOBILE HEALTHCARE DATA

(75) Inventors: Sheng Kim, Shanghai (CN); Declan Patrick Kelly, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 557 days.

(21) Appl. No.: 12/298,585

(22) PCT Filed: Apr. 24, 2007

(86) PCT No.: PCT/IB2007/051496
§ 371 (c)(1),
(2), (4) Date: Oct. 27, 2008

(87) PCT Pub. No.: WO2007/125473
PCT Pub. Date: Nov. 8, 2007

(65) Prior Publication Data
US 2009/0187421 A1    Jul. 23, 2009

(30) Foreign Application Priority Data
Apr. 28, 2006  (CN) .......................... 2006 1 0079935

(51) Int. Cl.
*G06Q 50/00*  (2012.01)
(52) U.S. Cl.
USPC .......................................................... 705/2
(58) Field of Classification Search
USPC ....................................................... 705/2, 3
See application file for complete search history.

(56) References Cited

U.S. PATENT DOCUMENTS

| | | | |
|---|---|---|---|
| 5,266,944 A * | 11/1993 | Carroll et al. | 340/573.4 |
| 5,772,586 A | 6/1998 | Heinonen et al. | |
| 6,485,418 B2 | 11/2002 | Yasushi et al. | |
| 6,524,239 B1 * | 2/2003 | Reed et al. | 600/300 |
| 7,103,578 B2 * | 9/2006 | Beck et al. | 705/75 |
| 7,390,299 B2 * | 6/2008 | Weiner et al. | 600/300 |
| 2002/0178126 A1 * | 11/2002 | Beck et al. | 705/75 |
| 2002/0188466 A1 * | 12/2002 | Barrette et al. | 705/2 |
| 2004/0044493 A1 * | 3/2004 | Coulthard | 702/122 |
| 2004/0153344 A1 * | 8/2004 | Bui et al. | 705/2 |
| 2005/0134459 A1 * | 6/2005 | Glick et al. | 340/572.1 |
| 2005/0177615 A1 | 8/2005 | Hawthorne et al. | |
| 2007/0219823 A1 * | 9/2007 | Warner | 705/2 |

FOREIGN PATENT DOCUMENTS

JP        2003150718 A      5/2003

OTHER PUBLICATIONS

Schwaibold M, et al: Key factors for personal health monitoring and diagnosis devices, 2002, pp. 143-148.

* cited by examiner

*Primary Examiner* — Gerald J. O'Connor
*Assistant Examiner* — Edward Winston, III

(57) ABSTRACT

An apparatus which configures a mobile healthcare network for monitoring a being includes a sender for sending the composition of the mobile healthcare network to a home healthcare network for monitoring the being and a receiver for receiving a configuration recommendation. The configuration recommendation corresponds to the composition of the mobile healthcare monitoring network and a medical history database of the home healthcare monitoring network An arranger arranges parameters of the mobile healthcare network according to the configuration recommendation.

18 Claims, 2 Drawing Sheets

MOBILE HEALTHCARE DATA

BACKGROUND OF THE INVENTION

This invention relates generally to the technology of monitoring healthcare data, and more particularly to monitoring healthcare data by a mobile healthcare network.

Recently more and more technologies have been proposed for monitoring personal healthcare data, and some of them are remotely monitoring by a mobile healthcare network deployed on/in a human body that could communicate with a central healthcare database.

The mobile healthcare network may include all kinds of biosensors performing all kinds of functions to detect health parameters of a person, such as blood pressure, pulse, blood fat, respiration and etc.

U.S. Pat. No. 6,485,418 B2 (Inventors: Mitsuo Yasushi, et al, assignee: Pioneer Corporation, Date of Patent: Nov. 26, 2002) discloses a healthcare monitoring system. The health monitoring system for communication between at least one terminal device that moves with a person whose health is monitored and a first center device. The terminal device detects health parameters of the person, and diagnoses of the condition of health of the person in accordance with a result of the detection, and transmits the result of the diagnosis to the first center device. The first center device stores the historical diagnosis information concerning the person, receives the result of the diagnosis from the terminal device, judges whether detailed data concerning the condition of health of the person is needed in accordance with the result of the diagnosis and the historical diagnosis information, and issues a request command of the detailed data to the terminal device when it judges that the detailed data is needed.

SUMMARY OF THE INVENTION

While how to make full use of both the data gathered by mobile healthcare network and the history data of the central database to make diagnoses has been substantively investigated, there is a need to have a smoother handover between a home healthcare network and a mobile healthcare network, especially when the composition of the mobile network varies from time to time.

It is a desire of the invention to provide an improved healthcare monitoring system that could address the above need.

The desire is addressed in an apparatus for configuring a mobile healthcare network of monitoring a being. The apparatus comprises a sender for sending the composition of the mobile healthcare network to a home healthcare network of monitoring the being, a receiver for receiving a configuration recommendation, the configuration recommendation corresponds to the composition of the mobile healthcare monitoring network and a history database of the home healthcare monitoring network, and an arranger for arranging setting parameters of the mobile healthcare network according to the configuration recommendation.

According to one embodiment of the invention, the apparatus further comprises a detector for detecting the composition of the mobile healthcare network. By adopting a configuration recommendation based on the composition of the mobile healthcare monitoring network and a history database of the home healthcare monitoring network, the parameters of the mobile healthcare network could be more adaptable and suitable to the current situation of the being.

The desire is also addressed by an apparatus for handing over an application of monitoring a being from a home healthcare network to a mobile healthcare network. The apparatus comprises a receiver for receiving the composition of the mobile healthcare network, a generator for generating a configuration recommendation according to the composition of the mobile healthcare network and a history database of the home healthcare network, and a sender for sending the configuration recommendation to the mobile healthcare monitoring network.

According to one embodiment of the invention, the composition of the mobile healthcare network includes the types of sensors deployed on/in the body of the being.

According to another embodiment of the invention, the composition of the mobile healthcare network further includes the quantity of each type of the sensors.

According to still another embodiment of the invention, the composition of the mobile healthcare network further includes the status of each of the sensors.

Other objects and attainments together with a fuller understanding of the invention will become apparent and appreciated by referring to the following description and claims in conjunction with the accompanying drawings.

BRIEF DESCRIPTION OF THE DRAWINGS

The invention is explained in further detail, and by way of examples, with reference to the accompanying drawings wherein.

Throughout the drawings, the same reference numerals indicate similar or corresponding features or functions.

DETAILED DESCRIPTION OF THE PREFERRED EMBODIMENTS

Figure 1:
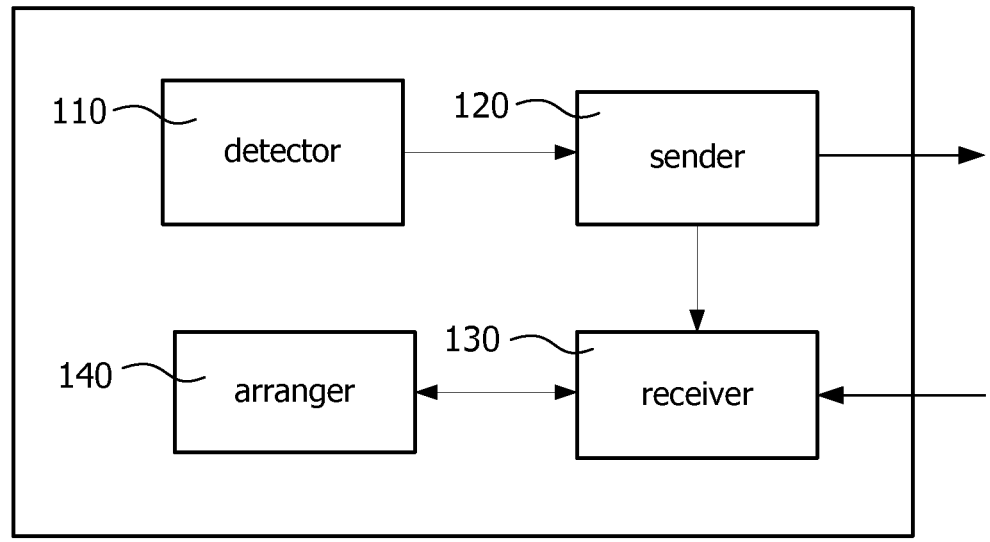
FIG. 1 is a schematic diagram of a configuration apparatus according to one embodiment of the invention.

FIG. 1 is a schematic diagram of a configuration apparatus according to one embodiment of the invention. The configuration apparatus 100 could be part of a mobile healthcare network.

When the human being under monitoring is at home, the home healthcare network takes care of the monitoring, which may have very abundant resources to carry out this task, such as a big history healthcare database, strong data processing capability, a large amount of sensors scattered in the home and on/in the body of the human being, and etc. When the human being under monitoring is out of his home (for example, in a park), the mobile healthcare network takes care of the monitoring, which may have limited resources to carry out this task, for example, only a few sensors are carried by the human being.

The mobile healthcare network could include all kinds of biosensors performing all kinds of functions to detect health parameters of a person, such as body temperature, blood pressure, pulse, blood fat, respiration and etc. It may also include all kinds of environment sensors which detect the environmental data of an environment a person is in, such as surrounding temperature, air pressure, humidity and etc.

The sensors of the mobile healthcare network could be deployed on/in the body of a human being under monitoring, or an animal being under monitoring. The sensors could be wireless connected to a mobile phone of the human being, and the mobile phone could communicate with a home healthcare network having a history healthcare database. Some environment sensors could also be physically incorporated into the mobile phone.

The mobile phone could be substituted by a specific mobile healthcare-monitoring device that is dedicated to manage the mobile healthcare network, as long as the mobile healthcare monitoring device could commutate with the sensors and the home healthcare network. The mobile healthcare monitoring device could have some capacity of data processing and data storage, and configuration apparatus 100 could be part of the mobile healthcare monitoring device.

Configuration apparatus 100 includes a sender 120, a receiver 130 and an arranger 140. It could further include a detector 110.

The sender 120 sends the composition of the mobile healthcare network to a home healthcare network of monitoring the human being. The composition of the mobile healthcare network could be obtained from the detector 110, and it could also be inputted manually via a user interface (not shown) of configuration apparatus 100.

The composition of the mobile healthcare network includes the types of sensors deployed on/in the body of the human being.

Each time when the human being under monitoring leaves the home healthcare network, there could be a different requirement of what kind of healthcare data should be collected. Accordingly the mobile network should include different set of sensors to achieve the requirement.

For example, last time a calorie sensor was included since the human being under monitoring wanted to know how many calories he would consume for his jogging in the park. This time a respiration sensor is included since the human being under monitoring is having a respiratory problem.

The composition of the mobile healthcare network further includes the quantity of each type of the sensors. For example, two pressure sensors (one under the left foot, and the other under the right foot) are included.

The composition of the mobile healthcare network further includes the status of each of the sensors. Each sensor may have different capacity/availability of data processing, data storing, communication and power.

The mobile healthcare network may have a dynamic combination of different types/amounts/status of sensors. It could have a basic set of sensors (for example, including a body temperate sensor, a pulse sensor), and have some optional sensor(s) selected based on a specific monitoring purpose.

The receiver 130 receives a configuration recommendation, and the configuration recommendation corresponds to the composition of the mobile healthcare monitoring network and a history database of the home healthcare monitoring network.

The configuration recommendation could includes some setting parameters of each sensor or each type sensor of the mobile healthcare network, such as sampling frequency, reporting frequency, reporting threshold of abnormal health data, and etc. For example, for a respiration sensor, sampling frequency is 1 time per 2 minutes under normal situation, reporting frequency is 1 time per 4 minutes under normal situation, reporting threshold of abnormal situation is 25 times of respiration per minutes if the human being under monitoring is not doing some exercises (other sensors may provide additional information of whether the human being is doing some exercises).

The configuration recommendation could be saved in a storage unit (not shown) of configuration apparatus 100 for future use. If next time the detector 110 does not find any changes of the composition of the mobile healthcare monitoring network, one possibility could be achieved by directly using the setting parameters instead of going through the whole configuration process again if the user does not want to take the history data into account.

The sender 120 and receiver 130 could be a part of any current or future wired/wireless communication device, such as internet connection, intranet connection, GSM, blue tooth, WiFi, and etc, as long as the mobile healthcare network and the home healthcare network could build up a communication channel and accomplish data transfer.

The arranger 140 arranges setting parameters of the mobile healthcare-monitoring network according to the configuration recommendation, so that each sensor could function as the configuration recommendation indicates.

For example, the respiration sensor will gather respiration data of the human being under monitoring every 2 minutes under normal situation, and report the gathered data to the home healthcare network every 4 minutes under normal situation, and if the respiration rate of the human being is more than 25 times per minute and the human being is not doing some exercises, the respiration sensor will report this abnormal situation to the human being and the home healthcare network.

The detector 110 detects the composition of the mobile healthcare network. The detector 110 may pro-actively send a message to search any member sensor is joining the mobile healthcare network, or it may passively receive a message pro-actively sent by a member sensor that will join the mobile healthcare network.

It is understandable that the home network of this embodiment could be any other places the human being under monitoring is living in other than his/her home, such as hospital ward, sanatorium, rest home and etc.

The desire of this invention can also be implemented by means of a suitably programmed computer provided with a computer program for configuring a mobile healthcare network of monitoring a being. The computer program product for configuring a mobile healthcare network of monitoring a being comprises code for sending the composition of the mobile healthcare network to a home healthcare network of monitoring the being, code for receiving a configuration recommendation, the configuration recommendation corresponds to the composition of the mobile healthcare monitoring network and a history database of the home healthcare network, and code for arranging setting parameters of the mobile healthcare network according to the configuration recommendation.

Such a computer program product may be stored in a storage carrier.

These portions of program code may be provided to a processor to produce a machine, such that the code that executes on the processor create means for implementing the functions specified as above.

Figure 2:
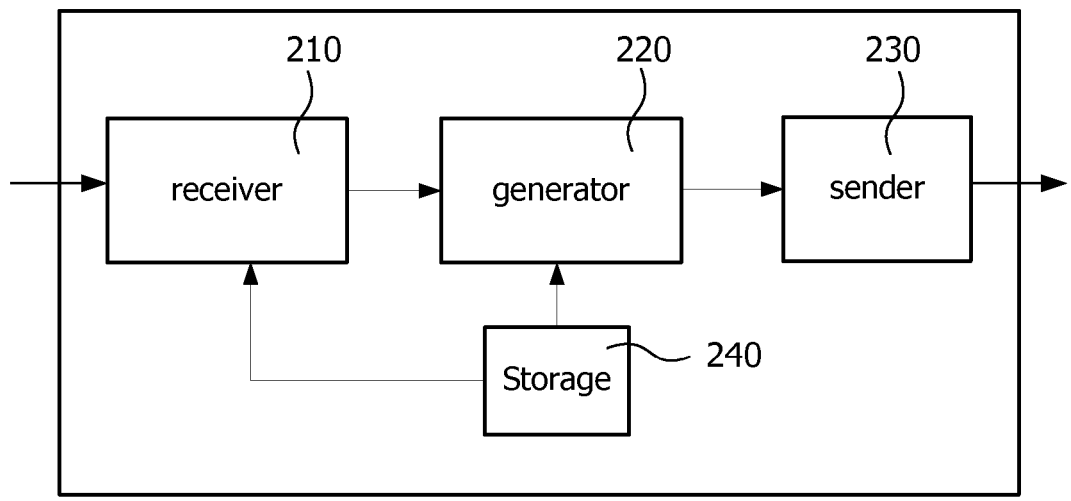
FIG. 2 is a schematic diagram of a handover apparatus according to another embodiment of the invention.

FIG. 2 is a schematic diagram of a handover apparatus according to another embodiment of the invention. The handover apparatus 200 could be a part of a home healthcare network.

When the human being under monitoring leaves his/her home, an application of monitoring the human being needs to be transferred from the home healthcare network to the mobile healthcare network carried by the human being.

The leaving activity of the human being could be detected by some sensors of the home healthcare network, such as a pressure sensor under the carpet of the main gate, or a motion camera installed above the main gate.

Handover apparatus 200 includes a receiver 210, a generator 220, and a sender. It could also include a storage unit 240.

The receiver 210 receives the composition of the mobile healthcare network. The composition of the mobile healthcare network includes the types of sensors deployed on/in the body of the being, and it may also include the quantity of each type of the sensors and/or the status of each of the sensors.

The generator 220 generates a configuration recommendation according to the composition of the mobile healthcare network and a history database of the home healthcare network.

The configuration recommendation varies not only with the changing data of the history healthcare database since it is frequently updated by fresh health data, but also with the different composition of the mobile healthcare network.

For example, if the history healthcare data indicate that the human being under monitoring is suffering a cardio problem, the sample frequency of the sensors relating to the heart of the mobile healthcare network should be increased to a higher level than the normal situation.

If a sensor with a big storage unit is included in the mobile healthcare network, the report frequency of the sensor could be reduced.

Also if the remaining power of one sensor is at a low level, its sampling frequency and reporting frequency could be reduced.

There are many other samples/rules that could reflect the relationship among the configuration recommendation and the composition of the healthcare network and the history healthcare data.

The sender 230 sends the configuration recommendation to the mobile healthcare monitoring network.

The receiver 210 and sender 230 could be a part of any current or future wired/wireless communication device, such as internet connection, intranet connection, GSM, blue tooth, WiFi, and etc, as long as the mobile healthcare network and the home healthcare network could build up a communication channel and accomplish data transfer.

Storage unit 240 stores the history healthcare data of the healthcare database. It is a non-volatile flash memory card. It could also be any other storage devices, such as a hard disk, a floppy disc and etc.

It is understandable the receiver 210 could also be a user input device, and the composition of the mobile healthcare network could be inputted manually via the receiver 210.

The desire of the invention can also be addressed by means of a suitably programmed computer provided with a computer program for handing over an application of monitoring a being from a home network to a mobile healthcare network. A computer program for handing over an application of monitoring a being from a home network to a mobile healthcare network comprises code for receiving the composition of the mobile healthcare network, code for generating a configuration recommendation according to the composition of the mobile healthcare network and a history database of the home healthcare network, and code for sending the configuration recommendation to the mobile healthcare monitoring network.

Such a computer program product may be stored in a storage carrier.

These portions of program code may be provided to a processor to produce a machine, such that the code that executes on the processor create means for implementing the functions specified as above.

Figure 3:
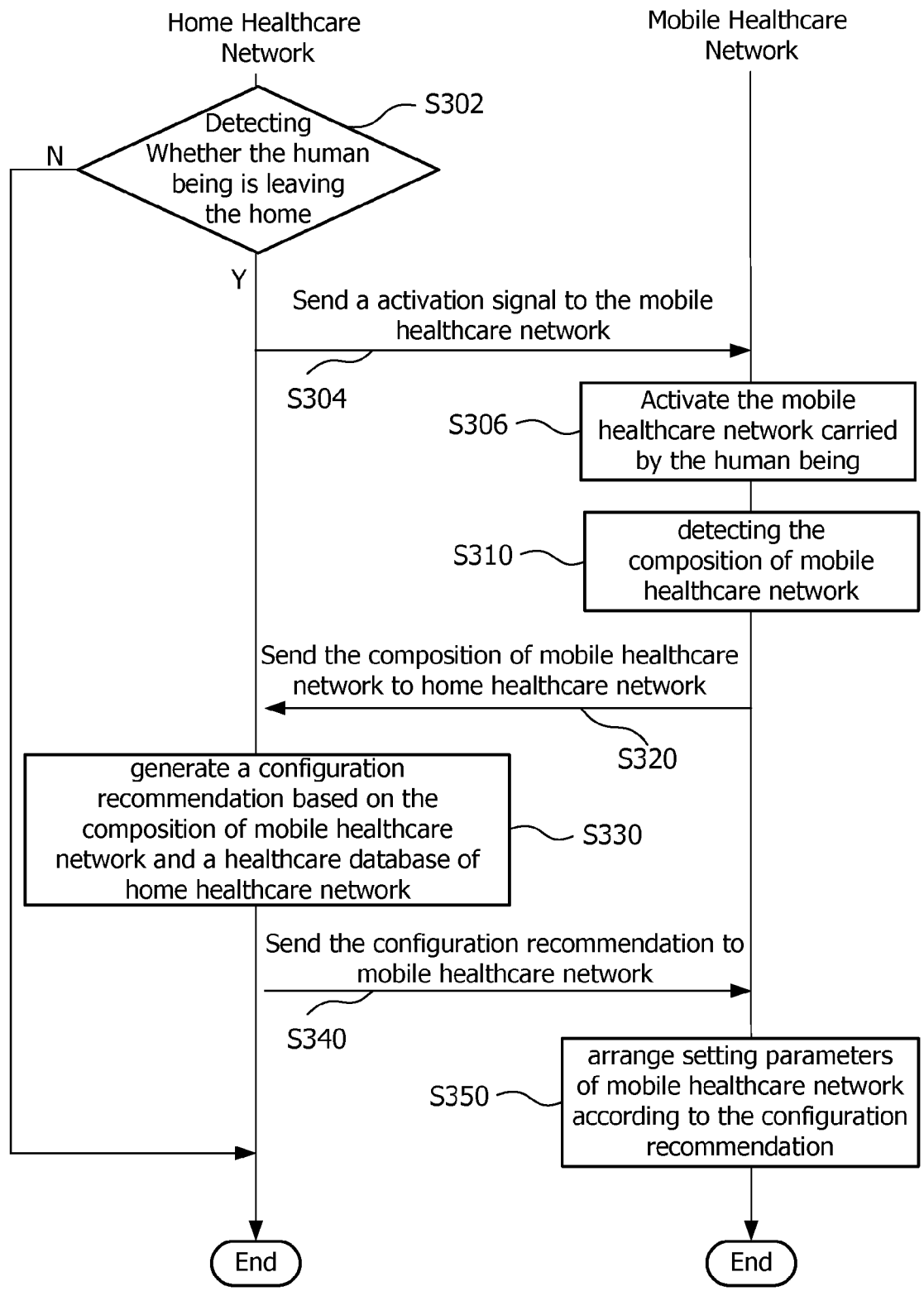
FIG. 3 is a flow chart illustrating a handover process between a home healthcare network and a mobile healthcare network according to another embodiment of the invention.

FIG. 3 is a flow chart illustrating a handover process between a home healthcare network and a mobile healthcare network according to another embodiment of the invention.

First, the home healthcare network detects whether the human being under monitoring is leaving the home (step S302). If yes, the home healthcare network sends an activation signal to the mobile healthcare network (step S304), then the mobile healthcare network carried by the human being is activated. (Step S306)

Then, The mobile home network detects its composition. (Step S310) The composition of the mobile healthcare network includes the types of sensors deployed on/in the body of the human being, and it may also include the quantity of each type of the sensors and/or the status of each of the sensors. And the composition of the mobile healthcare network is sent to the home healthcare network (Step S320).

After receiving the composition of the mobile healthcare network, the home network generates a configuration recommendation according to the composition of the mobile healthcare network and a history database of the home healthcare network (Step S330). Then the configuration recommendation is sent to the mobile healthcare network (Step S340).

Finally, the mobile healthcare network arranges the setting parameters of its sensors according to the configuration recommendation (Step S350), so that all sensors of the mobile healthcare network could function properly to carry out the monitoring application.

While the invention has been described in conjunction with specific embodiments, it is evident that many alternatives, modifications and variations will be apparent to those skilled in the art in light of the foregoing description. Accordingly, it is intended to embrace all such alternatives, modifications and variations as fall within the spirit and scope of the appended claims.

The invention claimed is:

1. A method for configuring a mobile healthcare network for monitoring a patient comprising:
with a home healthcare network:
when the patient is at home, monitoring health parameters of the patient with sensors scattered in a patient's home and sensors at least one of on or in the patient,
detecting when the patient is leaving home,
in response to detecting that the patient is leaving home, transferring monitoring the health parameters of the patient from the home healthcare network to a mobile healthcare network carried by the patient including activating the mobile healthcare network carried by the patient;
with the mobile healthcare network:
detecting a composition of sensors currently deployed at lest one of on or in the patient in the mobile healthcare network in response to detecting that the patient is leaving home,
sending the detected composition of the mobile healthcare network to the home healthcare network;
with the home healthcare network:
receiving the detected composition from the mobile healthcare network,
generating a configuration recommendation for the mobile healthcare network based on the received composition and on patient health information from a database of the home healthcare network, the configuration recommendation including setting parameters including at least one of sampling frequency, reporting frequency, and a reporting threshold for abnormal health data,
sending the generated configuration recommendation to the mobile healthcare network;
with the mobile healthcare network:
receiving the configuration recommendation, the configuration recommendation corresponding to the composition of the mobile healthcare network and the information from the database of the home healthcare network, and setting parameters of the mobile healthcare network according to the received configuration recommendation.

2. The method according to claim 1, further including:
when the patient is outside the home, with the mobile healthcare network:
sampling the health parameters of the patient monitored with the sensors at least one of on or in the patient, and
storing the sampled health parameters in a memory of the mobile healthcare network.

3. The method according to claim 2, further including:
with the mobile healthcare network;
sending the sampled health parameters stored in the memory of the mobile healthcare network to the home healthcare network;
with the home healthcare network:
receiving the sampled health parameters,
with a computer of the home healthcare network applying rules to the sampled health parameters to generate a revised configuration recommendation when the patient is outside the home, and
arranging the setting parameters of the mobile healthcare network according to the revised configuration recommendation.

4. The method according to claim 3, further including reducing a sampling frequency of one of the sensors if remaining power of the one sensor is at a low level.

5. An apparatus for configuring a healthcare system comprising:
a home healthcare network including at least one processor;
a mobile healthcare network including at least one processor;
wherein the processors of home and mobile healthcare networks are programmed to:
with the home healthcare network processor:
when the patient is at home, monitoring health parameters of the patient from sensors scattered in a patient's home and sensors at least one of on or in the patient,
detecting when the patient is leaving home,
in response to detecting that the patient is leaving home, transferring monitoring the health parameters of the patient from the home healthcare network to the mobile healthcare network carried by the patient including activating the mobile healthcare network carried by the patient;
with the mobile healthcare network processor:
detecting a composition of sensors currently deployed at least one of on or in the patient in the mobile healthcare network in response to detecting that the patient is leaving home,
sending the detected composition of the mobile healthcare network to the home healthcare network;
with the home healthcare network processor:
receiving the detected composition from the mobile healthcare network,
generating a configuration recommendation for the mobile healthcare network based on the received composition and on patient health information from a database of the home healthcare network, the configuration recommendation including setting parameters including at least one of sampling frequency, reporting frequency, and a reporting threshold for abnormal health data,
sending the generated configuration recommendation to the mobile healthcare network;
with the mobile healthcare network processor:
receiving the configuration recommendation, the configuration recommendation corresponding to the composition of the mobile healthcare network and the information from the database of the home healthcare network, and
setting parameters of the mobile healthcare network according to the received configuration recommendation.

6. A healthcare network including a home healthcare network which monitors the patient in the home and a mobile healthcare network which monitors the patient outside of the home, the mobile healthcare network comprising:
a biosensor configured to monitor health parameters of a person carrying the mobile healthcare network;
a transmitter configured to transmit signals wirelessly to a receiver of a home healthcare network;
a receiver configured to receive the signals from a transmitter of the home healthcare network; and
one or more processors programmed to in response to the home healthcare network handing over patient monitoring responsibility to the mobile healthcare network perform the following steps:
detecting a composition of the biosensor connected with the mobile healthcare network,
controlling the transmitter to send the detected composition to the home healthcare network, and
setting parameters of the mobile healthcare network according to a configuration recommendation received by the receiver from the home healthcare network.

7. The healthcare network according to claim 6, wherein the home healthcare network includes:
a plurality of sensors which monitors the health parameters of the patient when the patient is at home,
a home healthcare network receiver which receives the signals from the mobile healthcare network transmitter;
a home healthcare network transmitter which transmits the signals to the mobile healthcare network receiver;
a database which stores a health information history and configuration information; and
one or more processors programmed to:
generate a configuration recommendation for the activated mobile healthcare network based on a biosensor composition of the activated mobile healthcare network received by the home healthcare network receiver from the activated mobile healthcare network and the health information history and the configuration information stored in the database,
control the home healthcare network transmitter to send the generated configuration recommendation to the mobile healthcare network.

8. The healthcare network according to claim 7, wherein:
the one or more processors are further programmed to:
control the mobile healthcare network transmitter to send the monitored health parameters to the home healthcare network receiver; and
wherein the home healthcare network processor is further programmed to:
apply rules to the health parameters received by the home healthcare network receiver to generate a revised configuration recommendation based at least in part on the received health parameters; and controlling the home healthcare network transmitter to transmit the revised configuration recommendation to the mobile healthcare network receiver.

9. The healthcare network according to claim 8, wherein the mobile healthcare network processor is further programmed to:

arrange the setting parameters of the mobile healthcare network according to the revised configuration recommendation; and reduce a sampling frequency of a sensor in response to remaining power of the sensor being low.

10. The healthcare network according to claim 6, the configuration recommendation including setting parameters including at least one of sampling frequency, reporting frequency, and a reporting threshold for abnormal health data.

11. The healthcare network according to claim 6, wherein the mobile healthcare network processor is further programmed to:

store the health parameters monitored by the biosensor in a memory; controlling the mobile healthcare network transmitter to send the monitored health parameters to the home healthcare network receiver; and arrange the setting parameters of the mobile healthcare network according to the revised configuration recommendation.

12. A healthcare network including a home healthcare network and a mobile healthcare network, the home healthcare network comprising:

a plurality of sensors which monitor health parameters of the patient when the patient is at a home location;

a home healthcare network receiver which wirelessly receives health parameter signals from the mobile healthcare network transmitter when the patient is outside of the home location;

a home healthcare network transmitter which wirelessly transmits signals to a mobile healthcare network receiver;

a home healthcare network database which stores a health information history and configuration information; and a handover computer programmed to in response to the patient leaving the home location perform the steps of:

activating the mobile healthcare network, generating a configuration recommendation for the activated mobile healthcare network based on a biosensor of the activated mobile healthcare network composition received by the home healthcare network receiver from the activated mobile healthcare network and the health information history and the configuration information stored in the home healthcare network database, the configuration recommendation including setting parameters including at least one of sampling frequency, reporting frequency, and a reporting threshold for abnormal health data, controlling the home healthcare network transmitter to send the generated configuration recommendation to the activated mobile healthcare network.

13. The healthcare network according to claim 12, wherein the home healthcare network handover computer is further programmed to:

in response to changes in the received health parameters apply rules to the health parameters received by the home healthcare network receiver to generate a revised configuration recommendation based at least in part on the received health parameters; and controlling the home healthcare network transmitter to transmit the revised configuration recommendation to the mobile healthcare network receiver.

14. The healthcare network according to claim 13, wherein the home healthcare network handover computer is programmed to apply the rules by performing the steps of:

comparing the health parameters and an indication of remaining power received by the home healthcare receiver with corresponding thresholds; and wherein the revised configuration recommendation includes a changed sampling frequency.

15. A method of healthcare monitoring comprising:

when a patient is at home, monitoring the patient by monitoring a plurality of sensors which measure a plurality of health parameters of the patient with a home healthcare network;

in response to the patient leaving the home, handing over monitoring the patient to a mobile healthcare network;

after handing over monitoring the patient to the mobile healthcare network, with a biosensor of the mobile healthcare network which is worn by the patient, monitoring at least one of the health parameters of the patient;

transmitting at least one monitored the health parameter from the mobile healthcare network to the home healthcare network;

using the at least one monitored health parameter, generating a configuration recommendation with the home healthcare network;

transmitting the generated configuration recommendation from the home healthcare network to the mobile healthcare network;

configuring at least the mobile healthcare network and the biosensor in accordance with the configuration recommendation.

16. The method according to claim 15, wherein the configuration recommendation is performed by the home healthcare network and wherein the at least one health parameter monitored by the mobile healthcare network is communicated wirelessly from the mobile healthcare network to the home healthcare network and the configuration recommendations are transmitted wirelessly from the home healthcare network to the mobile healthcare network and further including:

changing the configuration recommendation with changes in the at least one monitored health parameters.

17. The method according to claim 15, wherein configuration recommendation includes a sampling frequency of the biosensor and a reporting frequency for transmitting the at least one monitored health parameter from the mobile healthcare network to the home healthcare network.

18. An apparatus for configuring a healthcare system comprising:

a home healthcare network including at least one processor;

a mobile healthcare network including at least one processor;

wherein the processors of home and mobile healthcare networks are programmed to perform the method of:

when a patient is at home, monitoring the patient by monitoring a plurality of sensors which measure a plurality of health parameters of the patient with the home healthcare network;

in response to the patient leaving the home, handing over monitoring the patient to the mobile healthcare network;

after handing over monitoring the patient to the mobile healthcare network, with a biosensor of the mobile healthcare network which is worn by the patient, monitoring at least one of the health parameters of the patient;

transmitting at least one monitored health parameter from the mobile healthcare network to the home healthcare network;

using the at least one monitored health parameter, generating a configuration recommendation with the home healthcare network;

transmitting the generated configuration recommendation from the home healthcare network to the mobile healthcare network;

configuring at least the mobile healthcare network and the biosensor in accordance with the configuration recommendation.

* * * * *